(12) United States Patent
Ikoma (10) Patent No.: US 11,523,770 B2
(45) Date of Patent: Dec. 13, 2022

(54) SYSTEMS AND METHODS FOR ITCH MONITORING AND MEASUREMENT

(71) Applicant: GALDERMA HOLDING SA, La Tour-de-Peilz (CH)

(72) Inventor: Akihiko Ikoma, Lausanne (CH)

(73) Assignee: GALDERMA HOLDING SA, Zug (CH)

( * ) Notice: Subject to any disclaimer, the term of this patent is extended or adjusted under 35 U.S.C. 154(b) by 650 days.

(21) Appl. No.: 15/893,278

(22) Filed: Feb. 9, 2018

(65) Prior Publication Data

US 2018/0228427 A1    Aug. 16, 2018

Related U.S. Application Data

(60) Provisional application No. 62/457,292, filed on Feb. 10, 2017.

(51) Int. Cl.
*A61B 5/00* (2006.01)
*A61B 5/11* (2006.01)
*A61B 5/024* (2006.01)

(52) U.S. Cl.
CPC .............. *A61B 5/445* (2013.01); *A61B 5/002* (2013.01); *A61B 5/02444* (2013.01);
(Continued)

(58) Field of Classification Search
CPC ..... A61B 5/445; A61B 5/002; A61B 5/02444; A61B 5/1123; A61B 5/1128;
(Continued)

(56) References Cited

U.S. PATENT DOCUMENTS

2004/0111040 A1* 6/2004 Ni .................. A61B 5/4806
600/534
2009/0099462 A1 4/2009 Almen
(Continued)

FOREIGN PATENT DOCUMENTS

GB    2 068 127 A    8/1981
JP    2004-261525 A    9/2004
(Continued)

OTHER PUBLICATIONS

Bulckaert, Arnoud, et al., "Heart rate-based nighttime awakening detection," European Journal of Applied Physiology, vol. 109, No. 2, (2010), pp. 317-322, XP019802940.
(Continued)

*Primary Examiner* — Devin B Henson
*Assistant Examiner* — Justin Xu
(74) *Attorney, Agent, or Firm* — Sunil Talapatra; Foley & Lardner LLP (57) ABSTRACT

A system for monitoring and measuring itch of a patient includes a wearable device including an actigraph sensor; and a controller electrically connected to the wearable device and including a processor and a memory. The wearable device is configured to measure, via the actigraph sensor, a movement of the patient; and send data indicative of the measured movement of the patient to the controller. The controller is configured to receive, via the processor, the data indicative of the measured movement; and determine, via the processor, a scratching movement of the patient based on the data indicative of the measured movement.

20 Claims, 4 Drawing Sheets

(52) U.S. Cl.
CPC .......... *A61B 5/1123* (2013.01); *A61B 5/1128* (2013.01); *A61B 5/4809* (2013.01); *A61B 5/681* (2013.01); *A61B 5/746* (2013.01); *A61B 5/024* (2013.01); *A61B 5/1118* (2013.01); *A61B 5/4842* (2013.01); *A61B 5/4848* (2013.01); *A61B 5/7282* (2013.01)

(58) Field of Classification Search
CPC ....... A61B 5/4809; A61B 5/681; A61B 5/746; A61B 5/7282; A61B 5/4848; A61B 5/4842; A61B 5/024; A61B 5/1118
See application file for complete search history.

(56) References Cited

U.S. PATENT DOCUMENTS

| | | | |
|---|---|---|---|
| 2010/0049066 A1 | 2/2010 | Hatakeyama | |
| 2010/0100004 A1 | 4/2010 | van Someren | |
| 2017/0245792 A1* | 8/2017 | Tversky | A61B 5/445 |
| 2018/0028106 A1* | 2/2018 | Leschinsky | A61B 5/1032 |

FOREIGN PATENT DOCUMENTS

| | | |
|---|---|---|
| JP | 2007-075428 A | 3/2007 |
| JP | 2009-131482 A | 6/2009 |
| JP | 2011-212441 A | 10/2011 |
| JP | 2014-039586 A | 3/2014 |
| JP | 2015-112152 A | 6/2015 |
| WO | WO-2016/108751 | 7/2016 |

OTHER PUBLICATIONS

International Preliminary Report on Patentability/Written Opinion issued in PCT/IB2018/050822 dated Aug. 13, 2019.

Petersen, Johanna, et al., "Actigraphy-Based Scratch Detection Using Logistic Regression," IEEE Journal of Biomedical and Health Informatics, vol. 17, No. 2, (2013), pp. 277-283, XP011496365.

Japanese Office Action issued for JP Appl. Ser. No. 2019-565076 dated Nov. 30, 2021 and English translation thereof (4 pages).

* cited by examiner

SYSTEMS AND METHODS FOR ITCH MONITORING AND MEASUREMENT

CROSS-REFERENCE TO RELATED PATENT APPLICATIONS

The present application claims priority to U.S. provisional application Ser. No. 62/457,292, filed Feb. 10, 2017, the entirety of which is hereby incorporated by reference.

BACKGROUND

Pruritus, or itch, is a common symptom of many dermatological diseases, such as atopic dermatitis and senile xerosis, and usually results in the act of scratching. For patients with certain conditions, such as patients with atopic dermatitis and patients with both Alzheimer's disease and senile xerosis, itching may also result in the patient experiencing a vicious itch-scratch cycle, where the patient exhibits the act of near-constant scratching to relieve the itching, which often significantly impairs a patient's quality of life.

Often, the severity of itchiness experienced by a patient is determined through self-assessment and reporting by the patient (e.g., through the use of a visual analogue scale). However, in some cases, the patient is unable to verbalize the amount of itching being experienced. Whether a given patient is experiencing itching and the severity of that itching is difficult to objectively evaluate.

SUMMARY

One method for estimating the severity of itching is through the use of an actigraph device. An actigraph device is worn by a patient and measures the motor activity produced by the patient due to the act of scratching. The device may then estimate the severity of itching experienced by the patient by quantifying the amount of scratching measured. However, this method requires a specially-developed device that measures the amount of scratching as a lump sum (e.g., the cumulative amount of hours during a given time period, such as during sleep, that the patient scratches) and provides the data after the fact, rather than in real time. In addition, in order to estimate the amount of scratching exhibited by the patient, the movement data collected by the device must be thereafter analyzed in view of a recorded scratching video in order to distinguish motor activity due to scratching from motor activity due to other types of movements.

Smart devices, such as mobile smart phones, smart tablets, or the like, are multifunctional devices that are capable of wirelessly communicating with peripheral wearable devices, such as watches or bracelets. The wearable devices are often capable of performing similar functions as the central smart device. In certain cases, the wearable device also includes one or more sensors, such as an actigraph sensor capable of capturing movements of a wearer.

By providing an actigraph sensor on a wearable device, the wearable device can measure the amount of scratching in real time and the duration and frequency of the scratching can be accurately captured to the second. With the real time detection of scratching, the wearable device can alert the user with a distraction (by, for example, deploying a signal such as a vibration) to break the itch-scratch cycle. Based on scientific evidence, it has been established that the itch-scratch cycle can be broken with a distraction.

According to an exemplary embodiment of the present disclosure, a system for monitoring and measuring itch of a patient includes a wearable device including an actigraph sensor; and a controller electrically connected to the wearable device and including a processor and a memory. The wearable device is configured to measure, via the actigraph sensor, a movement of the patient; and send data indicative of the measured movement of the patient to the controller. The controller is configured to receive, via the processor, the data indicative of the measured movement; and determine, via the processor, a scratching movement of the patient based on the data indicative of the measured movement.

According to one aspect of the system, the controller is also configured to measure an amplitude and a frequency of the data indicative of the measured movement, and the controller is also configured to determine whether the measured movement is a scratching movement based on the measured amplitude and the measured frequency.

According to another aspect of the system, the controller is also configured to determine whether the measured amplitude exceeds a predetermined amplitude and whether the measured frequency exceeds a predetermined frequency, and, if the measured amplitude exceeds the predetermined amplitude and the measured frequency exceeds the predetermined frequency, the controller is configured to determine that the measured movement is a scratching movement.

According to another aspect of the system, the wearable device is configured to alert the patient when the controller determines that the measured movement is a scratching movement.

According to another aspect of the system, the wearable device is configured to alert the patient with at least one of an auditory signal, a visual signal, and a tactile signal.

According to another aspect of the system, the wearable device also includes a heart rate sensor, the heart rate sensor is configured to measure a heart rate of the patient, and the controller is configured to determine a depth of sleep of the patient based on the measured heart rate.

According to another aspect of the system, a first time period is defined as a period between a first time, which is a time when an acceleration measured by the actigraph sensor is zero, and a second time, which is a next subsequent time when the acceleration measured by the actigraph sensor is zero, and a second time period is defined as a period between the second time and a third time, which is a next subsequent time when the acceleration measured by the actigraph sensor is zero, and the controller is configured to determine, via the processor, a scratching movement of the patient by determining that all of the following conditions are met: (1) a difference in a maximum absolute value of acceleration during the first time period and a maximum absolute value of acceleration during the second time period does not exceed a predetermined upper limit; (2) a difference in a length of time of the first time period and a length of time of the second time period does not exceed a predetermined upper limit; (3) a maximum absolute value of acceleration during the first time period is not less than a predetermined lower limit; (4) a length of time of the first time period does not exceed a predetermined upper limit; and (5) an error rate does not exceed a predetermined upper limit, the error rate being defined as a percentage of time periods among a predetermined number of previous time periods that fail to meet conditions (1) through (4).

According to another aspect of the system, the wearable device is a wrist-worn device.

According to another aspect of the system, the controller is located in an external device that is separate from the wearable device.

According to another aspect of the system, the external device is a mobile phone.

According to another aspect of the system, the wearable device is integral with the controller.

According to another exemplary embodiment of the present disclosure, a method for monitoring and measuring itch of a patient includes the steps of measuring, via a wearable device, a movement of the patient; sending, via the wearable device, data indicative of the measured movement of the patient to a controller; and determining, via the controller, a scratching movement of the patient based on the data indicative of the measured movement.

According to one aspect of the method, the step of measuring the data indicative of the measured movement includes measuring, via the controller, an amplitude of the data indicative of the measured movement; and measuring, via the controller, a frequency of the data indicative of the measured movement. The step of determining the scratching movement of the patient based on the data indicative of the measured movement includes determining the scratching movement of the patient based on the measured amplitude and the measured movement.

According to another aspect of the method, the step of determining the scratching movement of the patient based on the data indicative of the measured movement also includes determining, via the controller, whether the measured amplitude exceeds a predetermined amplitude; and determining, via the controller, whether the measured frequency exceeds a predetermined frequency. If the measured amplitude exceeds the predetermined amplitude and the measured frequency exceeds the predetermined frequency, the controller determines that the measured movement is a scratching movement.

According to another aspect, the method also includes alerting the patient, via the wearable device, when the controller determines that the measured movement is a scratching movement.

According to another aspect of the method, the wearable device alerts the controller via at least one of an auditory signal, a visual signal, and a tactile signal.

According to another aspect of the method, a first time period is defined as a period between a first time, which is a time when an acceleration measured by the actigraph sensor is zero, and a second time, which is a next subsequent time when the acceleration measured by the actigraph sensor is zero, and a second time period is defined as a period between the second time and a third time, which is a next subsequent time when the acceleration measured by the actigraph sensor is zero, and determining, via the controller, a scratching movement of the patient based on the data indicative of the measured movement includes determining that all of the following conditions are met: (1) a difference in a maximum absolute value of acceleration during the first time period and a maximum absolute value of acceleration during the second time period does not exceed a predetermined upper limit; (2) a difference in a length of time of the first time period and a length of time of the second time period does not exceed a predetermined upper limit; (3) a maximum absolute value of the acceleration during the first time period is not less than a predetermined lower limit; (4) a length of time of the first time period does not exceed a predetermined upper limit; and (5) an error rate does not exceed a predetermined upper limit, the error rate being defined as a percentage of time periods among a predetermined number of previous time periods that fail to meet conditions (1) through (4).

According to another aspect of the method, the wearable device is a wrist-worn device.

According to another aspect of the method, the controller is located in an external device that is separate from the wearable device.

According to another aspect of the method, the external device is a mobile phone.

BRIEF DESCRIPTION OF THE DRAWINGS

The details of one or more embodiments of the subject matter described in this specification are set forth in the accompanying drawings and the description below. Other features, aspects, and advantages of the subject matter will become apparent from the description, the drawings, and the claims.

DETAILED DESCRIPTION

Figure 1:
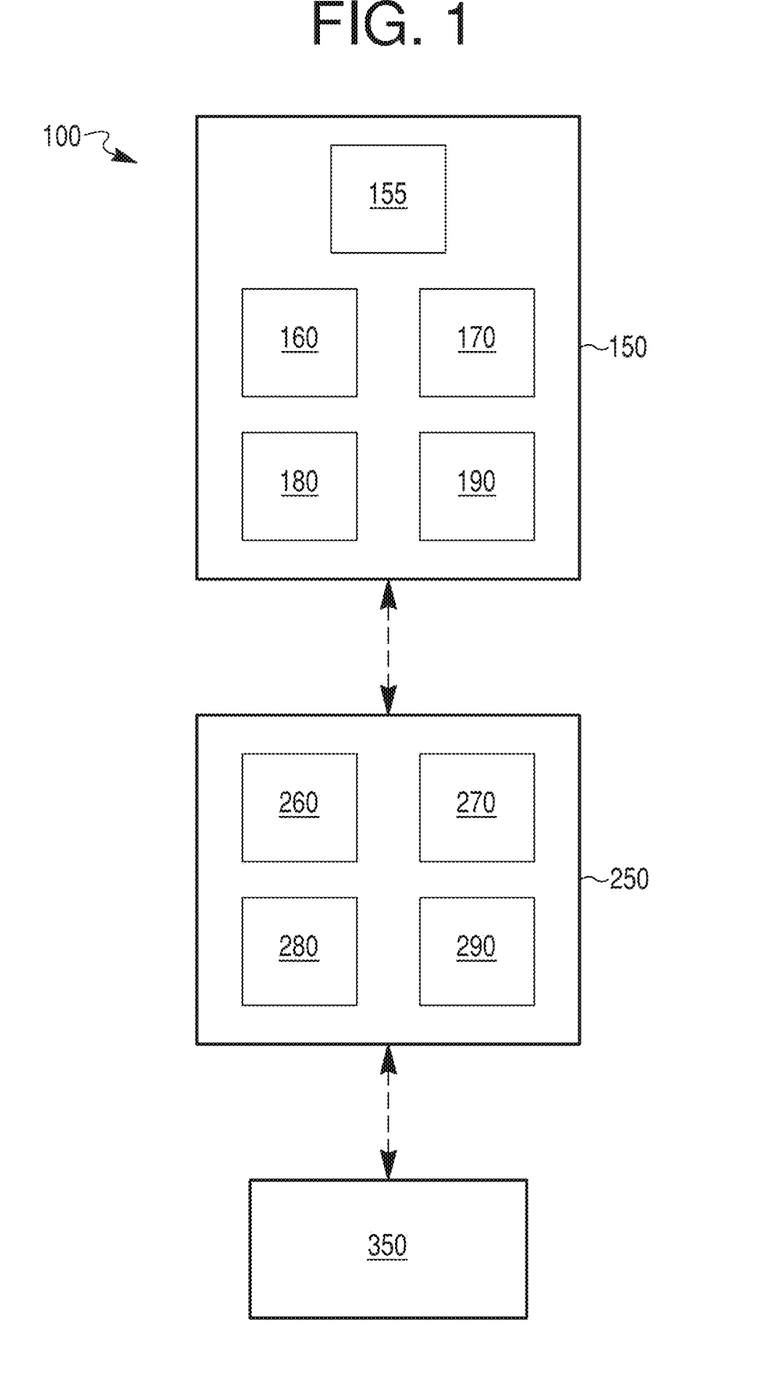
FIG. 1 shows a functional block diagram of a system for itch monitoring and measurement according to one embodiment.

FIG. 1 shows a system 100 for itch monitoring and measurement according to one embodiment. As shown in FIG. 1, system 100 includes a wearable device 150 and a controller 250. The wearable device 150 is electrically connected with the controller 250 such that the wearable device 150 can receive and/or send signals to the controller 250. In certain embodiments, the wearable device 150 is wirelessly connected with the controller 250. For example, the wearable device 150 includes a transceiver (not shown) configured to allow wireless communication between the wearable device 150 and the controller 250 and/or an external device. As one example, the transceiver is configured to operate using a frequency-hopping technique. According to one specific example, the transceiver is Bluetooth®-enabled and communicates with the controller 250 over a Bluetooth® link.

The wearable device 150 is configured to be worn by a user of the system 100, such as a patient (for example, a patient suffering from an itching condition). In certain embodiments, the wearable device 150 is a wrist-worn device. For example, the wearable device 150 is a smart watch, such as an Apple Watch, or a smart bracelet or the like. In certain embodiments, an external device includes the controller 250 such that the controller 250 is physically separate from the wearable device 150. For example, the controller 250 is a mobile communication device, such as a mobile phone, a tablet, a laptop computer, or the like. In other embodiments, however, the controller 250 is integrally provided with the wearable device 150.

As shown in FIG. 1, according to one aspect, the wearable device 150 includes one or more sensors 155, a processor 160, a memory 170, a device interface 180, and a display 190. In certain embodiments, the one or more sensors 155 include an actigraph sensor configured to detect a movement of the user or patient. In addition, in some embodiments, the one or more sensors 155 may also include additional sensors such as a heart rate sensor, which is configured to detect a heart rate, or pulse rate, of the user or patient. The memory 170 is configured to store machine instructions that, when executed by the processor 160, cause the processor 160 to perform operations to monitor and measure scratching movement and itch experienced by the user or patient, as will be described in further detail below. The memory 170 may also store data to effect presentation of one or more resources, content items, measurements, etc., via the display 190. The processor 160 may include a microprocessor, an application-specific integrated circuit (ASIC), a field-programmable gate array (FPGA), etc., or combinations thereof. The memory 170 may include, but is not limited to, electronic, optical, magnetic, or any other storage or transmission device capable of providing the processor 160 with program or machine instructions. The memory 170 may include a floppy disk, compact disc read-only memory (CD-ROM), digital versatile disc (DVD), magnetic disk, memory chip, read-only memory (ROM), random-access memory (RAM), Electrically Erasable Programmable Read-Only Memory (EEPROM), erasable programmable read only memory (EPROM), flash memory, optical media, or any other suitable memory from which the processor 160 can read instructions. The instructions may include code from any suitable computer programming language such as, but not limited to, ActionScript®, C, C++, C#, HTML, Java®, JavaScript®, Perl®, Python®, Visual Basic®, and XML.

As also shown in FIG. 1, the controller 250 includes a processor 260, a memory 270, a device interface 280, and a display 290. The memory 270 is configured to store machine instructions that, when executed by the processor 260, cause the processor 260 to perform operations to monitor and measure scratching movement and itch experienced by the user or patient, as will be described in further detail below. The memory 270 may also store data to effect presentation of one or more resources, content items, measurements, etc., via the display 290. The processor 260 may include a microprocessor, an application-specific integrated circuit (ASIC), a field-programmable gate array (FPGA), etc., or combinations thereof. The memory 270 may include, but is not limited to, electronic, optical, magnetic, or any other storage or transmission device capable of providing the processor 260 with program or machine instructions. The memory 270 may include a floppy disk, compact disc read-only memory (CD-ROM), digital versatile disc (DVD), magnetic disk, memory chip, read-only memory (ROM), random-access memory (RAM), Electrically Erasable Programmable Read-Only Memory (EEPROM), erasable programmable read only memory (EPROM), flash memory, optical media, or any other suitable memory from which the processor 260 can read instructions. The instructions may include code from any suitable computer programming language such as, but not limited to, ActionScript®, C, C++, C#, HTML, Java®, JavaScript®, Perl®, Python®, Visual Basic®, and XML.

Figure 2:
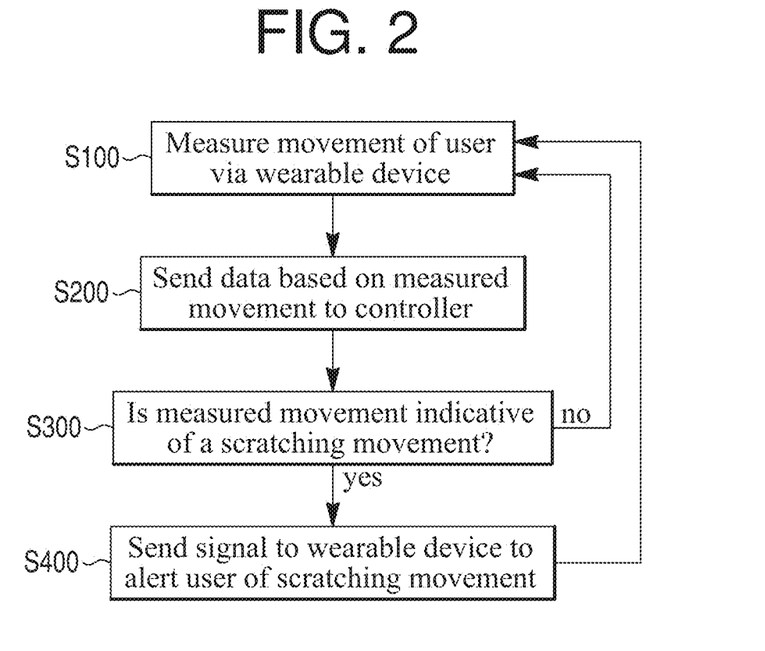
FIG. 2 is a flow diagram showing a method of detecting a scratching movement using the system of FIG. 1.

FIG. 2 shows a flow diagram of a method used to measure and monitor itch according to one embodiment. As noted above, the wearable device 150 includes an actigraph sensor 155 that is configured to detect a movement of the user or patient. As shown in FIG. 3, in a step S100, movement of the user or patient is measured using the actigraph sensor 155 of the wearable device 150. Data indicative of the movement detected by the actigraph sensor 155 may be stored in the memory 170 and sent via the device interface 180 to the controller 250 in a step S200. In certain embodiments, the wearable device 150 is configured to continuously send, in real time (e.g., on a second-by-second basis), the data indicative of the movement detected by the actigraph sensor 155 to the controller 250 via the device interface 180. In certain other embodiments, the wearable device 150 is configured to store the data indicative of the movement detected by the actigraph sensor 155 in the memory 170 and send the data indicative of the movement to the controller 250 after an entire body of data indicative of the movement has been measured and stored in the memory 170. After a predetermined amount of time (for example, a period corresponding to a user or patient's entire sleep session), the wearable device 150 is configured to send the data indicative of the movement detected by the actigraph sensor 155 to the controller 250.

Figure 3A:
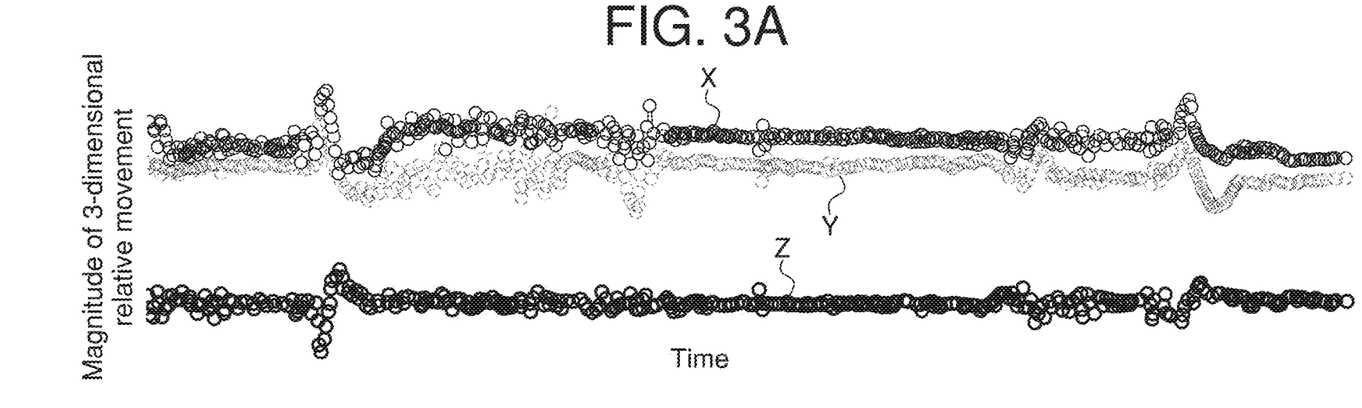
FIG. 3A is a graphical representation showing data indicative of a non-scratching movement according to an embodiment.
Figure 3B:
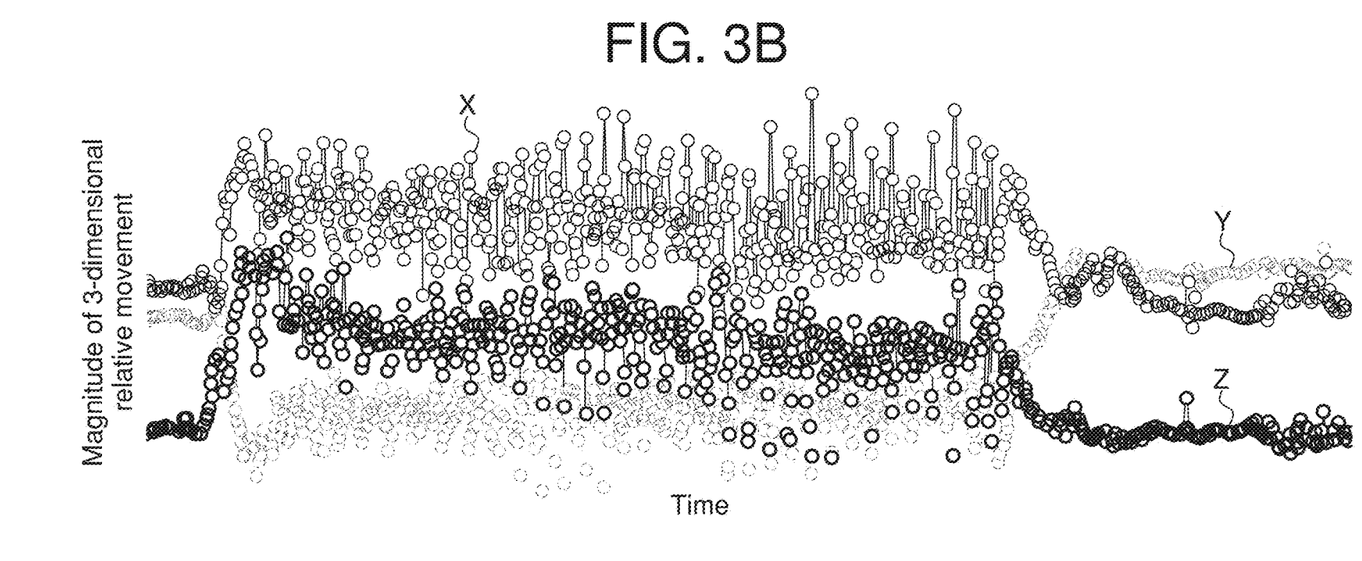
FIG. 3B is a graphical representation showing data indicative of a scratching movement according to an embodiment.

In a step S300, the controller 250, via the device interface 280, receives the data indicative of the measured movement and determines, via the processor 260, whether the movement constitutes a scratching movement based on the received data. For example, FIGS. 3A and 3B show examples of data indicative of measured movement received by the controller 250. As shown in FIGS. 3A and 3B, the data includes the relative movement of the wearable device 150 as moved by the user or patient. In certain embodiments, the relative movement is measured in a three-coordinate system (e.g., X, Y, and Z coordinates, as shown in FIGS. 3A and 3B). The controller 250, via the processor 260, may be configured to measure an amplitude of the relative movement of the wearable device 150 in one or more of the three coordinates and determine whether the amplitude exceeds a predetermined amplitude in one or more of the three coordinates. In addition, the controller 250 may be also configured to measure a frequency of the amplitude of the relative movement that exceeds the predetermined amplitude and determine whether the frequency exceeds a predetermined frequency in one or more of the three coordinates. If the measured amplitude does not exceed the predetermined amplitude and/or if the measured frequency does not exceed the predetermined frequency (i.e., NO at step S300), the controller 250 may be configured to determine that the user or patient is exhibiting non-scratching behavior (e.g., non-scratching movement), such as shown in FIG. 3A. As shown in FIG. 2, the method proceeds to step S100 and continues to measure movement of the user or patient via the wearable device 150. If the measured amplitude exceeds the predetermined amplitude and the measured frequency exceeds the predetermined frequency (i.e., YES at step S300), the controller 250 may be configured to determine that the user or patient is exhibiting scratching movement, such as shown in FIG. 3B. As shown in FIG. 2, the method proceeds to a step S400, in which the system 100 alerts the user or patient to the scratching behavior, as described in more detail below. The method then proceeds to step S100 and continues to measure movement of the user or patient via the wearable device 150. In the embodiments in which the wearable device 150 is configured to send the data indicative of the movement detected by the actigraph sensor 155 to the controller 250 after a predetermined period of time has elapsed, the controller 250 is configured to determine that the user or patient is exhibiting scratching movement after the predetermined period of time has elapsed and the data indicative of the movement detected by the actigraph sensor 155 has been received by the controller. Accordingly, in such embodiments, the controller 250 is configured to determine a timing and duration of the scratching movement after the predetermined period of time has elapsed.

Figure 4:
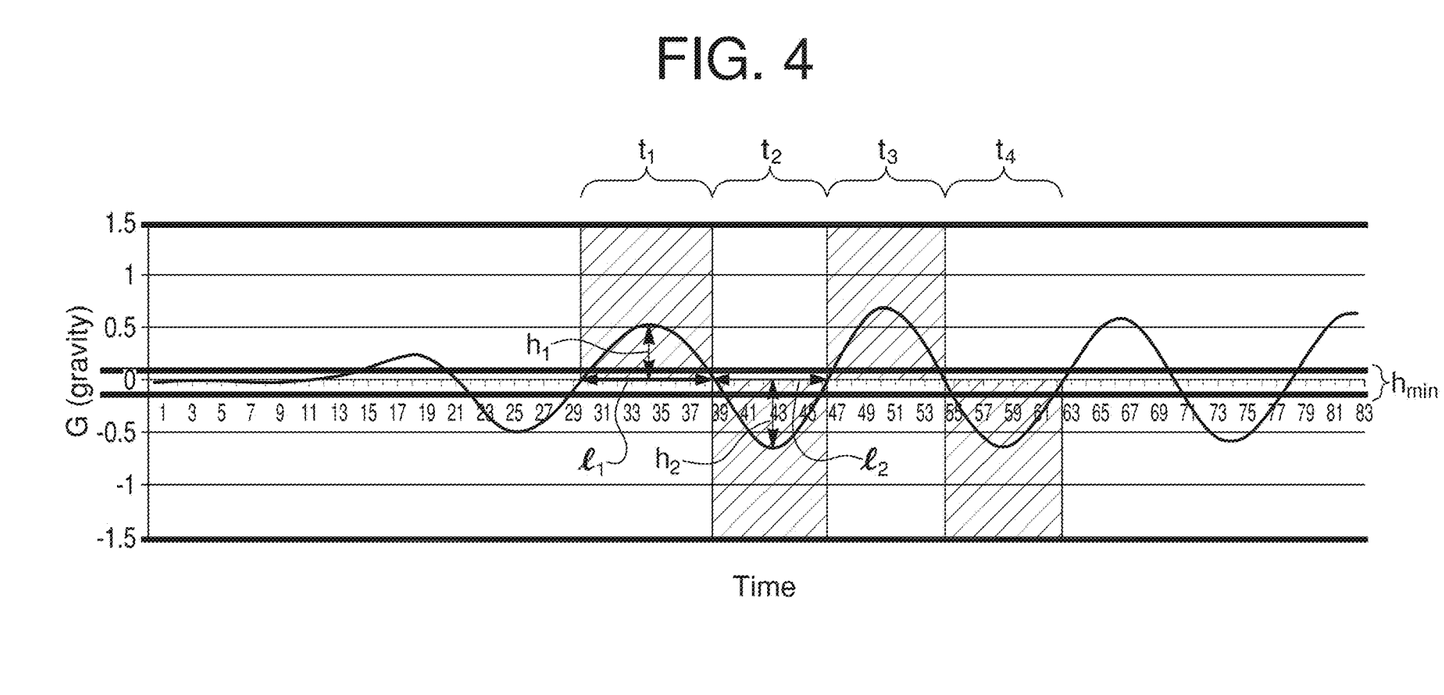
FIG. 4 is a chart illustrating an algorithm used by the method shown in FIG. 2.

FIG. 4 graphically illustrates an algorithm used to determine if the user or patient is engaged in scratching. The data indicative of the measured movement (for example, accelerometer data in three dimensional space) are the independent variables on which the algorithm bases calculations. The controller computes a time-course of acceleration based on a number of consecutive time periods. A first time period, such as time period $t_1$ shown in FIG. 4, is defined as a period between a first time, which is a time when an acceleration measured by the actigraph sensor is zero, and a second time, which is a next subsequent time when the acceleration measured by the actigraph sensor is zero. A second time period, such as time period $t_2$ shown in FIG. 4, is defined as a period between the second time and a third time, which is a next subsequent time when the acceleration measured by the actigraph sensor is zero. According to the algorithm, scratching is considered to be ongoing if all of the following predetermined conditions are met: (1) a difference in a maximum absolute value of acceleration during a time period and an immediately subsequent time period (shown as the difference between $h_1$ and $h_2$ in FIG. 4) does not exceed a predetermined upper limit; (2) a difference in a length of a time period and an immediately subsequent time period (shown as the difference between $l_1$ and $l_2$ in FIG. 4) does not exceed a predetermined upper limit; (3) a maximum absolute value of acceleration during a time period is not under a predetermined lower limit (shown as $h_{min}$ in FIG. 4); (4) a length of a time period does not exceed a predetermined upper limit; and (5) an error rate, defined as a percentage of time periods among a predetermined number of previous time periods (for example, time periods $t_1$, $t_2$, $t_3$, and $t_4$ shown in FIG. 4) that fail to meet conditions (1) through (4). Additionally, the algorithm relies on two additional predetermined conditions to determine when a scratching begins and when the scratching ends. Scratching is considered to have started if the acceleration values continuously meet all of the conditions (1) through (5) beyond a predetermined minimum time duration. Scratching is considered to have ended if the acceleration values do not meet any of the conditions (1) through (5) during a predetermined minimum number of consecutive time periods.

The algorithm accordingly allows for a highly reliable, real time detection of scratching by a user or patient. Combined with stimulation features (as described herein), the real-time detection of scratching provides to the user or patient an immediate response to distract the user or patient from scratching.

In certain embodiments, if scratching movement is determined by the controller 250, the controller 250 may be also configured to determine the amount of scratching movement performed over a period of time. For example, the controller 250 may be configured to determine the amount of time the user or patient exhibits scratching behavior from a point in time in which scratching behavior was exhibited to first begin (e.g., at a given point in time, the controller 250 determines that the user or patient has scratched for a certain amount of time). Based on the movement determined by the controller 250 (e.g., whether the controller 250 determines that the user or patient is exhibiting non-scratching movement or scratching movement), the controller 250 may determine whether the movement indicates that the user or patient is experiencing itching. In some embodiments, the controller 250 is also configured to determine a severity of a scratching movement performed by the user or patient (e.g., minimal scratching, moderate scratching, severe scratching) based on the measured amplitude and the measured frequency of the scratch. Based on the determination of the severity of the scratch, the controller 250 may be configured to determine the severity of itching that the user or patient is experiencing.

As noted above, the one or more sensors 155 of the wearable device 150, for example, also includes a heart rate sensor 170 configured to detect a heart rate of the user or patient. Data indicative of the heart rate detected by the heart rate sensor 155 may be stored in the memory 170 and sent via the device interface 180 to the controller 250. In certain embodiments, the wearable device 150 is configured to continuously send, in real time, the data indicative of the heart rate detected by the heart rate sensor 155 to the controller 250 via the device interface 180.

In certain embodiments, the controller 250, via the device interface 280, receives the data indicative of the measured heart rate and determines, via the processor 260, whether the heart rate indicates that the user or patient is sleeping (e.g., whether the heart rate indicates a sleep depth of the user or patient). In this case, the controller 250 can monitor the amount of scratching (as determined by the received data indicative of the movement detected by the actigraph sensor 155 of the wearable device 150) performed by the user or patient during a period of sleep. The controller 250 may be also configured to store the data indicative of the movement detected by the actigraph sensor 155 during the period of sleep as determined by the data indicative of the measured heart rate, in which the user or patient may later view via the display 290.

In some embodiments, the wearable device 150 is configured to provide a signal to the user or patient to indicate that the user or patient is engaging in scratching behavior (e.g., step S400 as shown in FIG. 2). According to one aspect, the signal is configured to distract the user or patient such that the user or patient stops engaging in scratching behavior. The signal is, for example, at least one of an auditory signal, a visual signal, and/or a tactile signal. For example, if the controller 250 determines that the user or patient is engaging in scratching movement, the controller 250 sends a signal, via the device interface 280, to the wearable device 150 to alert the user or patient by emitting a sound, a light, and/or a vibration. For example, upon receiving a signal from the controller 250 to alert the user or patient, the wearable device 150 may alert the user or patient with a graphical display via the display 190 and/or a sound or alarm. By providing such alerts to the user or patient, the user's attention is lessened on the itch, thereby reducing the amount of scratching and breaking the itch-scratch cycle.

In certain embodiments, and as also shown in FIG. 1, the controller 250, via the device interface 280, is configured to communicate with a central server 350 via a network, such as the Internet. The controller 250, via the device interface 280, may be configured to send movement data that may be stored on the central server 350. The central server 350 may be accessed to view scratching behavior over more time periods. For example, a physician may access the central server 350 to view scratching behavior to determine, monitor, and/or alter treatment for itching.

The controller 250 may be also configured to provide a user interface, via the display 290, which may be configured to allow the user or patient to enter, view, and/or change data relating to the system 100. For example, the user interface may allow the user or patient to enter profile data regarding the user or patient. The profile data may include information relevant to the user's current conditions relevant to itch. For example, the user or patient may enter profile data that indicates the user's demographic information (e.g., age, gender, race, etc.), medical history, dermatological conditions (e.g., whether the user or patient has atopic dermatitis), levels of itching experienced, skin care routine (e.g., extent of use of moisturizer), current skin conditions (e.g., scar evaluation, extent of dry skin), and other relevant medical information (e.g., whether the user or patient has Alzheimer's disease, medications). In addition, the user interface may also allow the user or patient to monitor progress of treatment of itch. For example, the user interface may allow the user or patient to view scratching behavior over a select period of time (e.g., over a day, a month, a year, etc.) to view patterns in scratching during the time period. The user interface may also allow the user or patient to control (e.g., start and/or stop) when the wearable device 150 measures the user's movement. For example, the user interface allows the user or patient to indicate when the user or patient is going to sleep, allowing the system 100 to begin measuring the movement of the user or patient for scratching behavior.

The system and methods described herein allow for the measurement and monitoring itch by providing for real-time measurement of scratching movement. By measuring and analyzing scratching movement of a user or patient, itching experienced by the user or patient can be objectively evaluated and treated in real-time. This allows for the treatment of itching in a user or patient having conditions that cause severe itch-scratch cycles and/or conditions that prevent the user or patient from verbalizing the extent of itching experienced. In addition, the system 100 is useable in combination with other treatment methods. For example, the system 100 is useable in conjunction with anti-itch drugs and can thereby improve the efficacy of such drugs. The system 100 also allows the user or patient and/or the user's physician to objectively monitor the progress and/or efficacy of the drug treatment.

While this specification contains many specific implementation details, these should not be construed as limitations on the scope of what may be claimed, but rather as descriptions of features specific to particular implementations. Certain features described in this specification in the context of separate implementations can also be implemented in combination in a single implementation. Conversely, various features described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated in a single software product or packaged into multiple software products embodied on tangible media.

References to "or" may be construed as inclusive so that any terms described using "or" may indicate any of a single, more than one, and all of the described terms.

Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

The claims should not be read as limited to the described order or elements unless stated to that effect. It should be understood that various changes in form and detail may be made by one of ordinary skill in the art without departing from the spirit and scope of the appended claims. All implementations that come within the spirit and scope of the following claims and equivalents thereto are claimed.

What is claimed is:

1. A system for monitoring and measuring itch of a patient, comprising:
   a wearable device comprising an actigraph sensor; and
   a controller electrically connected to the wearable device and comprising a processor and a memory,
   wherein the wearable device is configured to:
      measure, via the actigraph sensor, a movement of the patient; and
      send data indicative of the measured movement of the patient to the controller;
   wherein the controller is configured to:
      receive, via the processor, the data indicative of the measured movement;
      determine, via the processor, a scratching movement of the patient in real time responsive to the data indicative of the measured movement satisfying each of the following conditions (1)-(5):
         (1) a difference in a maximum absolute value of acceleration during a first time period and a maximum absolute value of acceleration during a second time period does not exceed a predetermined upper limit;
         (2) a difference in a length of time of the first time period and a length of time of the second time period does not exceed a predetermined upper limit;
         (3) the maximum absolute value of acceleration during the first time period is not less than a predetermined lower limit;
         (4) a length of time of the first time period does not exceed a predetermined upper limit; and
         (5) an error rate does not exceed a predetermined upper limit, the error rate being defined as a percentage of time periods among a predetermined number of previous time periods that fail to meet conditions (1) through (4),
   wherein the first time period is a period between a first time, which is a time when acceleration measured by the actigraph sensor is zero, and a second time, which is a next subsequent time when the acceleration measured by the actigraph sensor is zero, and the second time period is a period between the second time and a third time, which is a next subsequent time when the acceleration measured by the actigraph sensor is zero,
   wherein the controller is further configured to (i) receive, via an interface, an indication from the patient of when the patient is going to sleep and then commence measuring of the movement of the patient, and (ii) alert the patient in response to a determination relating to the measured movement, and wherein the predetermined number of previous time periods include at least the first time period, the second time period, a third time period following the second time period, and a fourth time period following the third time period.

2. The system of claim 1, wherein the controller is further configured to measure an amplitude and a frequency of the data indicative of the measured movement, and
wherein the controller is further configured to determine whether the measured movement is a scratching movement based on the measured amplitude and the measured frequency.

3. The system of claim 2,
wherein the controller is further configured to determine whether the measured amplitude exceeds a predetermined amplitude and whether the measured frequency exceeds a predetermined frequency, and
wherein, if the measured amplitude exceeds the predetermined amplitude and the measured frequency exceeds the predetermined frequency, the controller is configured to determine that the measured movement is a scratching movement.

4. The system of claim 1, wherein the wearable device is configured to alert the patient when the controller determines that the measured movement is a scratching movement.

5. The system of claim 4, wherein the wearable device is configured to alert the patient with at least one of an auditory signal, a visual signal, and a tactile signal.

6. The system of claim 1,
wherein the wearable device further comprises a heart rate sensor,
wherein the heart rate sensor is configured to measure a heart rate of the patient, and
wherein the controller is configured to determine a depth of sleep of the patient based on the measured heart rate.

7. The system of claim 1, wherein the wearable device is a wrist-worn device.

8. The system of claim 1, wherein the controller is located in an external device that is separate from the wearable device.

9. The system of claim 8, wherein the external device is a mobile phone.

10. The system of claim 1, wherein the wearable device is integral with the controller.

11. A method for monitoring and measuring itch of a patient, comprising:
measuring, via a wearable device comprising an actigraph sensor, a movement of the patient;
sending, via the wearable device, data indicative of the measured movement of the patient to a controller; and
determining, via the controller, a scratching movement of the patient responsive to the data indicative of the measured movement satisfying each of the following conditions (1)-(5):
(1) a difference in a maximum absolute value of acceleration during a first time period and a maximum absolute value of acceleration during a second time period does not exceed a predetermined upper limit;
(2) a difference in a length of time of the first time period and a length of time of the second time period does not exceed a predetermined upper limit;
(3) the maximum absolute value of acceleration during the first time period is not less than a predetermined lower limit;
(4) a length of time of the first time period does not exceed a predetermined upper limit; and
(5) an error rate does not exceed a predetermined upper limit, the error rate being defined as a percentage of time periods among a predetermined number of previous time periods that fail to meet conditions (1) through (4),
wherein the first time period is a period between a first time, which is a time when acceleration measured by the actigraph sensor is zero, and a second time, which is a next subsequent time when the acceleration measured by the actigraph sensor is zero, and the second time period is a period between the second time and a third time, which is a next subsequent time when the acceleration measured by the actigraph sensor is zero, and
receiving, via an interface, an indication from the patient of when the patient is going to sleep and then commencing measuring of the movement of the patient, and alerting the patient in response to a determination relating to the measured movement, and
wherein the predetermined number of previous time periods include at least the first time period, the second time period, a third time period following the second time period, and a fourth time period following the third time period.

12. The method of claim 11, wherein the step of measuring the data indicative of the measured movement comprises:
measuring, via the controller, an amplitude of the data indicative of the measured movement; and
measuring, via the controller, a frequency of the data indicative of the measured movement, and
wherein the step of determining the scratching movement of the patient based on the data indicative of the measured movement comprises determining the scratching movement of the patient based on the measured amplitude and the measured movement.

13. The method of claim 12, wherein the step of determining the scratching movement of the patient based on the data indicative of the measured movement further comprises:
determining, via the controller, whether the measured amplitude exceeds a predetermined amplitude; and
determining, via the controller, whether the measured frequency exceeds a predetermined frequency,
wherein, if the measured amplitude exceeds the predetermined amplitude and the measured frequency exceeds the predetermined frequency, the controller determines that the measured movement is a scratching movement.

14. The method of claim 11, further comprising:
alerting the patient, via the wearable device, when the controller determines that the measured movement is a scratching movement.

15. The method of claim 14, wherein the wearable device alerts the controller via at least one of an auditory signal, a visual signal, and a tactile signal.

16. The method of claim 11, wherein the wearable device is a wrist-worn device.

17. The method of claim 11, wherein the controller is located in an external device that is separate from the wearable device.

18. The method of claim 17, wherein the external device is a mobile phone.

19. A system for monitoring and measuring itch of a patient, comprising:
a wearable device comprising an actigraph sensor; and
a controller electrically connected to the wearable device and comprising a processor and a memory, wherein the wearable device is configured to:
  measure, via the actigraph sensor, a movement of the patient; and
  send data indicative of the measured movement of the patient to the controller;
wherein the controller is configured to:
  receive, via the processor, the data indicative of the measured movement;
  determine, via the processor, a scratching movement of the patient in real time responsive to the data indicative of the measured movement satisfying each of the following conditions (1)-(5):
    (1) a difference in a maximum absolute value of acceleration during a first time period and a maximum absolute value of acceleration during a second time period does not exceed a predetermined upper limit;
    (2) a difference in a length of time of the first time period and a length of time of the second time period does not exceed a predetermined upper limit;
    (3) the maximum absolute value of acceleration during the first time period is not less than a predetermined lower limit;
    (4) a length of time of the first time period does not exceed a predetermined upper limit; and
    (5) an error rate does not exceed a predetermined upper limit, wherein the error rate comprises a percentage of time periods among a predetermined number of previous time periods that fail to meet conditions (1) through (4),
wherein the first time period is a period between a first time, which is a time when acceleration measured by the actigraph sensor is zero, and a second time, which is a next subsequent time when the acceleration measured by the actigraph sensor is zero, and the second time period is a period between the second time and a third time, which is a next subsequent time when the acceleration measured by the actigraph sensor is zero,
wherein the controller is further configured to (i) receive, via an interface, an indication from the patient and then commence measuring of the movement of the patient, and (ii) alert the patient in response to a determination relating to the measured movement, and
wherein the predetermined number of previous time periods include at least the first time period, the second time period, a third time period following the second time period, and a fourth time period following the third time period.

20. The system of claim 19, wherein the interface is configured to allow the patient to control commencement of measuring of the movement of the patient.

* * * * *